US009372157B1

(12) United States Patent
Todd et al.

(10) Patent No.: US 9,372,157 B1
(45) Date of Patent: Jun. 21, 2016

(54) METHOD FOR NON-INVASIVE DETERMINATION OF CHEMICAL PROPERTIES OF AQUEOUS SOLUTIONS (75) Inventors: Paul W. Todd, Greenville, IN (US); Alan Jones, Campellsburg, IN (US); Nathan A. Thomas, Louisville, KY (US)

(73) Assignee: Techshot, Inc., Greenville, IN (US)

( * ) Notice: Subject to any disclaimer, the term of this patent is extended or adjusted under 35 U.S.C. 154(b) by 988 days.

(21) Appl. No.: 13/174,124

(22) Filed: Jun. 30, 2011

Related U.S. Application Data (62) Division of application No. 11/379,918, filed on Apr. 24, 2006, now abandoned.

(60) Provisional application No. 60/673,961, filed on Apr. 22, 2005.

(51) Int. Cl.
G01N 33/00 (2006.01)
G01N 21/80 (2006.01)
G01N 21/25 (2006.01)
G01N 21/31 (2006.01)

(52) U.S. Cl.
CPC .............. *G01N 21/80* (2013.01); *G01N 21/255* (2013.01); *G01N 21/314* (2013.01); *G01N 2201/0642* (2013.01)

(58) Field of Classification Search
USPC .......... 436/164; 73/53.01; 356/432, 436, 440, 356/229, 234; 204/403.01
See application file for complete search history.

(56) References Cited

U.S. PATENT DOCUMENTS

| 4,906,249 A | 3/1990 | Fogt et al. |
| 5,039,492 A | 8/1991 | Saaski et al. |
| 5,047,208 A | 9/1991 | Schweitzer et al. |
| 5,115,811 A | 5/1992 | Hartlaub et al. |
| 2008/0285036 A1* | 11/2008 | Hafeman et al. .............. 356/433 |

OTHER PUBLICATIONS

Jie Lin, Dong Liu, An Optical pH sensor with a linear response over a broad range, Analytica Chimica Acta Journal, copyright 2000, pp. 49-55, 408, Elsevier Science B.V., USA.
Zhihong Liu, Junfeng Liu, Tianlu Chen, Phenol red immobilized PVA membrane for an optical pH sensor with two determination ranges and long-term stability, Sensors and Actuators B Journal, copyright 2004, pp. 311-316, 107, Elsevier Science B.V., USA.
Miao Yuqing, Chen Jianrong, Fang Keming, New technology for the detection of pH, Journal of biochemical and biophysical methods, copyright 2005, pp. 1-9, 63, Elsevier Science B.V., USA.

(Continued)

*Primary Examiner* — Monique Cole
(74) *Attorney, Agent, or Firm* — Middleton Reutlinger; Robert H. Eichenberger; Chad D. Bruggeman (57) ABSTRACT A method for non-invasively determining a chemical property of an aqueous solution is provided. The method provides the steps of providing a colored solute having a light absorbance spectrum and transmitting light through the colored solute at two different wavelengths. The method further provides the steps of measuring light absorbance of the colored solute at the two different transmitted light wavelengths, and comparing the light absorbance of the colored solute at the two different wavelengths to determine a chemical property of an aqueous solution.

12 Claims, 9 Drawing Sheets

(56) References Cited

OTHER PUBLICATIONS

Antony S. Jeevarajan, Sundeep Vani, Thomas D. Taylor, Melody M. Anderson, Continuous pH Monitoring in a Perfused Bioreactor System Using an Optical pH Sensor, Biotechnology and Bioengineering Journal, copyright 2002, pp. 467-472, vol. 78, No. 4, Wiley Periodicals, Inc., USA.

Wang et al. Fast and Long Term Optical Sensors for pH Based on Sol-Gels; Analytica Chimica Acta, vol. 495 (2003) pp. 45-50.

* cited by examiner

METHOD FOR NON-INVASIVE DETERMINATION OF CHEMICAL PROPERTIES OF AQUEOUS SOLUTIONS

CROSS-REFERENCE TO RELATED APPLICATIONS

This application is a divisional application of, and claims priority to and benefit under 35 U.S.C. §120 to copending U.S. patent application Ser. No. 11/379,918, filed on Apr. 24, 2006, which claims priority to and benefit under 35 U.S.C. §119(e) to U.S. Provisional App. No. 60/673,961, filed on Apr. 22, 2005, the entire contents of the aforementioned applications are herein incorporated by reference.

STATEMENT REGARDING FEDERALLY SPONSORED RESEARCH OR DEVELOPMENT

This invention was made with support from the U.S. Government under contract NAS 9-01135 awarded by NASA. Pursuant to this contract, the government may have certain rights in this invention.

BACKGROUND

1. Field of the Invention

This application is in the general field of analytical chemistry, and more specifically, it is a device and method of use in the field of analytical biochemistry and cell culture. This invention provides an innovative method for measuring the hydrogen ion concentration in aqueous solutions, or the negative logarithm of the hydrogen ion concentration ("pH").

2. Background

Cell cultures are very sensitive to the pH of cell culture media, and monitoring and control of the media acidity are required for optimized cell growth. The object of the present invention is to provide a method for measuring pH of a solution without drawing a sample and without making contact with the solution thereby potentially contaminating it.

There are very few off-the-shelf available pH measurement systems that can provide fast, accurate, reliable, non-invasive measurement techniques and can be used for the automated monitoring and control of medium pH. The determination of pH currently requires that a sample be drawn from the solution, at which time one of three testing methods can be used. In one method, an electrochemical or optical pH probe is placed into the fluid, and a digital readout is obtained. This method requires a significant amount of solution to be drawn, and the testing process can contaminate the solution. Furthermore, highly accurate equipment can be expensive. The second method is less expensive and requires that a drop of solution be placed on filter paper impregnated with a colorimetric reagent so that a user can visually compare the color change to a reference chart. Although this method is inexpensive and requires little wasted sample, it is neither accurate nor precise, and it cannot be automated. In the third common method, a measured amount of color indicating solution is added to a measured amount of solution sample. This process is similar to the method using indicator paper in that its accuracy depends on the user's ability to discern color contrasts. The color indicating solution technique also requires that a significant amount of fluid be drawn for testing and then contaminated with the color change solution so that it is no longer useful for scientific purposes.

Thus, disadvantages of current pH test methods include the following: 1) a sample of the solution must be taken and exposed to a test device (pH probe, indicator paper, indicator chemicals, etc.), which potentially contaminates the sample and makes it unusable, resulting in wasted fluid; 2) color indicator paper and chemicals provide low accuracy and precision due to their reliance on the visual judgment of the user; 3) probe systems often exhibit short life span; 4) the probe system is the only technique that lends itself to automated controls; and 5) all of these methods are invasive.

The present invention provides a method for measuring pH of a solution without drawing a sample and without making contact with the solution (and thereby potentially contaminating it). The present invention thereby overcomes all of these disadvantages.

Although using the absorption of different wavelengths of light to determine pH is not a novel concept, the present invention comprises a method for data sampling and monitoring that is novel. Specifically, the present invention utilizes an absorbance ratio principle not used in prior art and an electronic means of automatic measurement and reporting.

The invention is especially useful in the field of cell culture, where culture media often contain pH indicator dyes. The invention is a useful replacement for immersible pH probes, which must interact directly with the liquid. It is an object of the present invention to avoid contact with cell culture liquids, which must be kept sterile and which can foul immersible devices that depend on chemical reactions.

BRIEF SUMMARY

Numerous fields of modern technology require the rapid measurement of solution characteristics using absorption spectrophotometry. A particular case in point is the determination of the pH of cell culture medium that contains a pH indicator, but various other applications are possible, including the use of spectrophotometry to determine redox potentials. In one redox application, for example, the extent of heme oxidation is measured using one of four possible absorbance ratios, since oxyhemoglobin has two isosbestic points—one at 523 nm and one at 588 nm. Thus, a sensitive measurement of heme's oxidation state would be possible by using the ratio of absorbance at 565 nm (using a green LED) to that at 670 nm (using a red LED).

The pH reader concept of the present invention utilizes at least two light-emitting diodes (LEDs) of different wavelengths and a photodiode to measure the pH of a solution that contains phenol red or another color-based pH indicator. The pH reader determines the acidity by transmitting the LED light through the solution and using the ratio of the light energy absorbed at the at least two wavelengths to determine the pH. The pH reader is capable of measuring pH in typical cell culture containers, including, but not limited to, petri dishes, T-flasks, test tubes, 96 microwell plates, Opticells® (commercially available transparent cell culture containers) and the like.

The present invention pH reader comprises a holder that shields the solution container from ambient light, an illuminator mounted within the holder that transmits light through the sample, and a photodetector within the holder that is capable of measuring light absorbance at a minimum of two different wavelengths. A bar-code reader or other means of automatic sample identification and electronics for recording and displaying pH, time, and sample number are optional. The design of the present invention takes full advantage of the spectral characteristics of phenol red solutions during pH changes. The acid form of phenol red absorbs light having a wavelength of 440 nm, and the base form of phenol red absorbs light having a wavelength of 560 nm. The ratio of absorbance at these two wavelengths can be used to determine pH and other chemical properties of a substance. These two peaks are separated by an isosbestic point, which is the wavelength at which the acid and base species have identical absorptive optical properties. The ratio of absorbance at the two peaks remains constant at a given pH, so this approach ensures a self-calibrated reading. The present pH reader differs from that presented by Jeevarajan et al., for example, because the Jeevarajan's pH reader uses spectral intensities at green (510 nm) and red (650 nm) wavelengths so that the pH calibration depends on the absolute height of phenol red's absorption peak at 560 nm, while the 440 nm peak is unused. The absolute height of phenol red's absorption peak at 560 nm is dependent on the concentration of phenol red, so it is necessary to know the concentration of phenol red when calibrating a device using the method of Jeevarajan. In comparison, the present invention relies on the ratio of absorbance between the peaks at 560 nm and 440 nm, which is not dependent on phenol red's concentration.

The present pH reader can also integrate a bar code scanner or similar means of identification that stores the serial number from a sample, and this information is stored in the on-board memory along with the samples' associated pH, plus the date and time of the scan.

Figure 1:
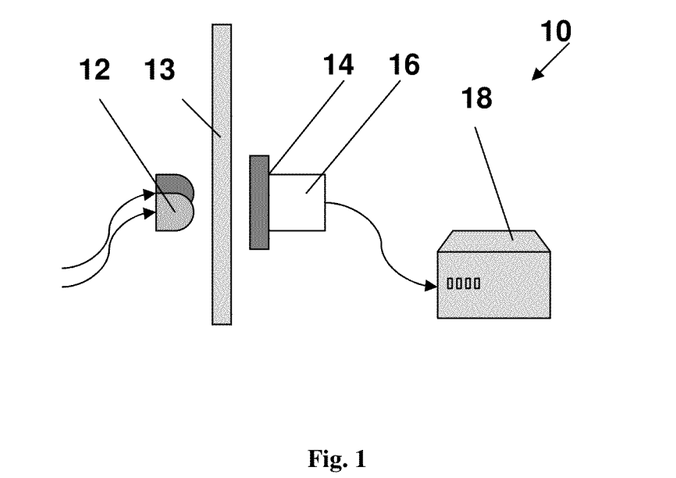
FIG. 1 is a diagram representing the principle components of an embodiment of the invention.

The present pH reader can operate in either of two modes: reflective and transmissive. In the reflective mode, the LEDs and sensor are mounted on the same circuit board and are aimed in the same direction. The photosensor then detects each of the individually switched LED wavelengths after the emitted light traverses the clear container, reflects from a mirror, traverses back through the clear container, and finally reaches the photosensor face. This configuration is physically compact but very sensitive to optical alignment. In the transmissive mode, as illustrated in FIG. 1, the LED's and photosensor circuit are on opposite sides of the sample solution and facing each other, although typically not on the same circuit board. In this configuration, the light is emitted from the LED, through the clear container, and directly on the photosensor. This configuration, though not as compact, is much more forgiving in its sensitivity to optical alignment.

Accordingly, a particular embodiment is a method for non-invasively determining a chemical property of an aqueous solution is provided that provides a container having an interior portion and an exterior portion. The method further provides, in the interior portion of the container, a colored solute having a light absorbance spectrum. The method also provides a holder that shields the container from ambient light. Yet another step provides at least one illuminator at the exterior portion of the container and transmitting light through the container with the at least one illuminator. A photodiode is provided and the light absorbance of the colored solute is measured at two different wavelengths. A ratio of the light absorbance of the colored solute at the two different wavelengths is used to determine a chemical property of an aqueous solution.

Another particular embodiment is a method for non-invasively determining a chemical property of an aqueous solution is provided that provides a container having an interior portion and an exterior portion. The method further provides, in the interior portion of the container, a colored solute having a light absorbance spectrum. The method also provides a step of shielding the container from ambient light and illuminating the colored solute at at least two separate wavelengths of light from the exterior of the container, and detecting the light absorbance of the colored solute at the at least two separate wavelengths at the exterior portion of the container. Converting the two light absorbances of the colored solute at the at least two separate wavelengths into a ratio and using that ratio to determine a chemical property of an aqueous solution.

Yet another particular embodiment that provides a method for non-invasively determining a chemical property of an aqueous solution is provided that provides a colored solute having a light absorbance spectrum and transmitting light through the colored solute at two different wavelengths. The method further provides the steps of measuring light absorbance of the colored solute at the two different transmitted light wavelengths, and comparing the light absorbance of the colored solute at the two different wavelengths to determine a chemical property of an aqueous solution.

Figure 2:
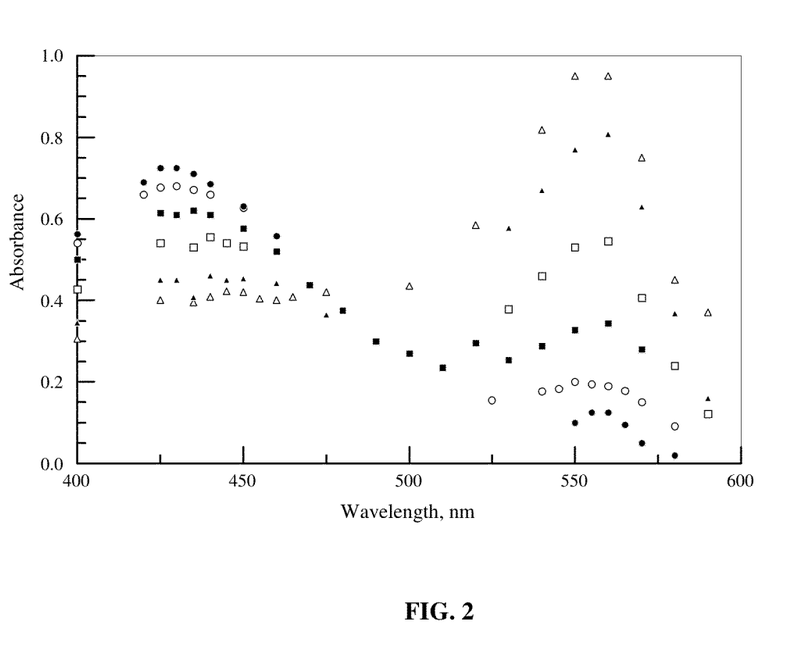
FIG. 2 is a graph showing absorbance spectra of phenol red in culture medium at seven pH's between 6.1 and 8.8 determined using a standard spectrophotometer.

The absorption spectrum of certain pH indicators consists of the combined absorption spectra of the ionized and non-ionized dye species in solution. Typically, the ionized and non-ionized species absorb light of different wavelengths, and their relative concentrations depend on hydrogen-ion concentration, which is expressed as pH (i.e., the negative common logarithm of H+ concentration). The ratio of the two absorbances is relatively independent of concentration of the indicator in the solution. The graphs showing absorption spectra of phenol red at several pH values are presented in FIG. 2.

BRIEF DESCRIPTION OF THE DRAWINGS

The present invention can take many physical embodiments and can assume many arrangements of components for carrying out the teachings of the invention, all of which may be appreciated by a person of skill in the art. The teachings of the present invention can be readily understood by considering the following detailed description of a preferred embodiment in conjunction with the accompanying drawings of said embodiment, in which.

DETAILED DESCRIPTION

While the present invention will be described more fully hereinafter with reference to the accompanying drawings in which particular embodiments and methods are shown, it is to be understood from the outset that persons of ordinary skill in the art may modify the invention herein described while achieving the functions and results of this invention. Sound engineering judgment may be used to modify various aspects and components of the invention without detracting from the broad, general teachings hereof. Accordingly, the description that follows is to be understood as illustrative and exemplary of specific embodiments within the broad scope of the present invention and not as limiting the scope of the invention. In the following descriptions, like numbers refer to similar features or like elements throughout.

The theory of the present invention, pH reader, is based upon the optical properties of solutions containing phenol red. The absorption maxima at 430 nm and 560 nm for phenol red in aqueous solution (Eagle's MEM) have a systematic dependence of the ratio of these absorbencies on pH. By shining a light source with these wavelengths through a solution containing phenol red, a photo detector positioned on the opposite side is able to measure the light not absorbed by the phenol red solution. The ratio of the measured light intensities of the two wavelengths subsequently can be processed to determine the pH of the solutions.

An embodiment of the present pH reader 10 is shown in FIG. 1 and consists of two printed circuit boards, one for the light source 12 and the other for the photo detector 14. Optical measurements are made by placing the light source on one side of a transparent sample container 13 and directing its output towards a photo detector 14 on the opposite side of said transparent sample container 13 in which is disposed a sample of liquid containing a pH indicating dye.

Peripheral equipment can be varied. In some laboratory applications, the electronic output 16 can be transmitted to a bioreactor control computer 18. In proposed spaceflight applications, the pH reader is integrated into multi-container cell culture systems. A vertical holder is envisioned for reading pH of T-flask cultures and Opticell® cultures while a horizontal holder is needed for 96-well-plate formats and petri dishes. For the consumer market, a test-tube holder is used, and peripheral materials include a supply of concentrated indicator solution, test tubes and transfer pipets.

The apparatus 10 is robust. It can be powered by a UL-approved DC converter as used for a variety of hand-held electronic devices. There are no fluid-contacting surfaces to clean or corrode. The electro-optical components have lifetimes measured in years at the anticipated output requirements. The pH reader does not require any routine maintenance. The pH reader is reliable as long as the optics (housed internally and not routinely exposed to any contaminant) are kept free of contamination and as long as the LEDs and photodiode do not change position relative to one another. Testing has verified that particulate (latex microspheres) in the sample solution will not affect the pH reading, and it was determined that the physical principles behind the testing are sufficiently robust to tolerate this type of fluid contamination. The pH Reader is an extremely safe method for measuring pH. It is a low power device, has no moving parts, no dangerous chemicals, no thermal issues, and no pressurized components.

Figure 11:
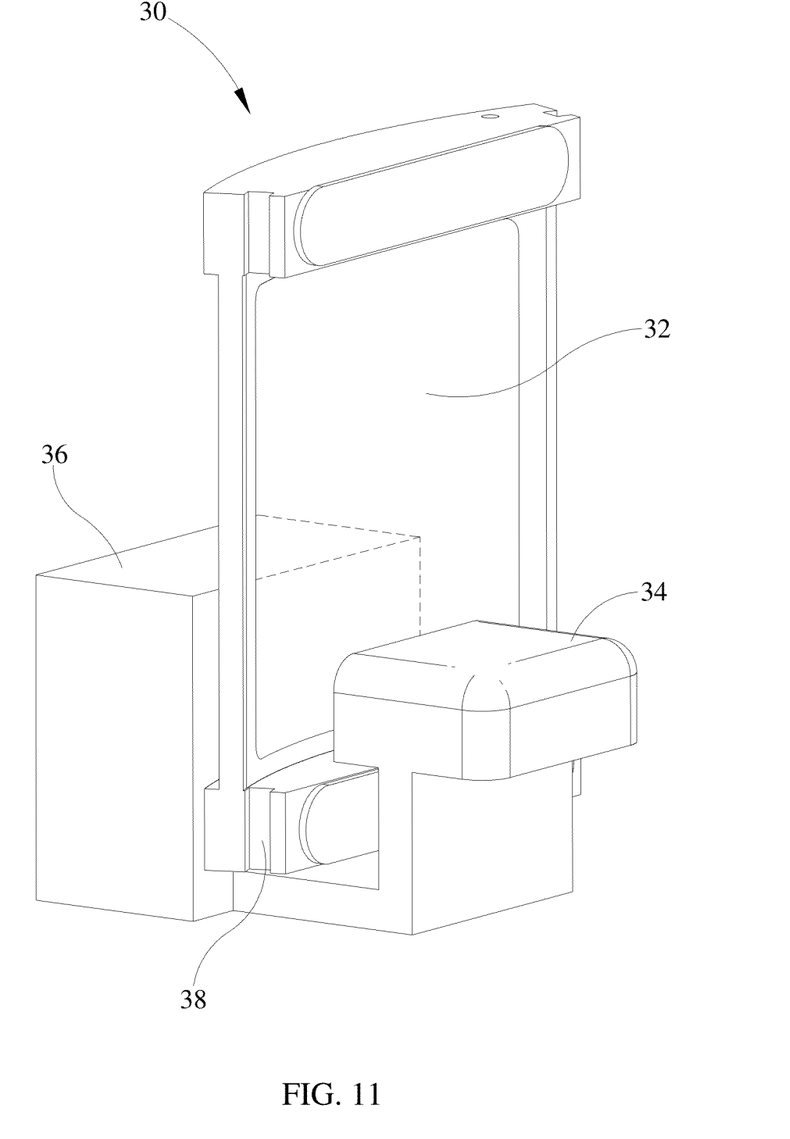
FIG. 11 is an embodiment of a pH reader of the invention.

FIG. 11 shows an embodiment of a pH reader 30 of the invention. This embodiment includes a transparent cell culture container 32, which is the sample, an illuminator housing 34 containing light-emitting diodes, and a detector housing 36 containing a photodiode and electronics. This embodiment further includes an automatic translation system 38 for culture vessels attached to a carousel or moving belt.

Figure 12:
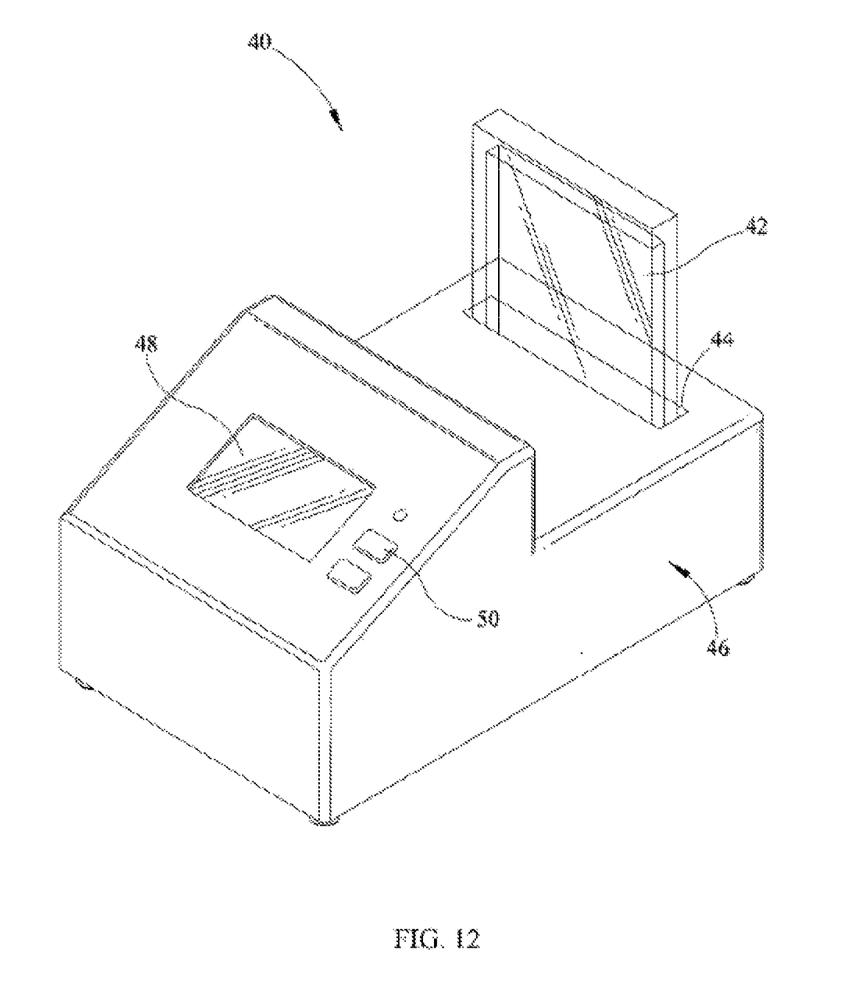
FIG. 12 is another embodiment of a pH reader of the invention.

FIG. 12 shows another embodiment of a pH reader 40 of the invention. The embodiment includes a housing 46 for the electronics and optics of the pH reader. The housing has a slot 44. A culture vessel 42 can be inserted into the slot 44, which houses the optical components of the pH reader 40 and can optionally include a bar code reader for reading bar codes on the culture vessels 42. The face of the pH reader has a digital display 48 that shows various information, including the status of the reader, the sample number, pH, time and date, and the graphical user interface options and commands. The user can control the reader and display by manipulating control buttons 50.

EXAMPLES

Example 1

Absorption Spectra of Phenol Red, a pH Indicator Dye, in Cell Culture Medium

Figure 3:
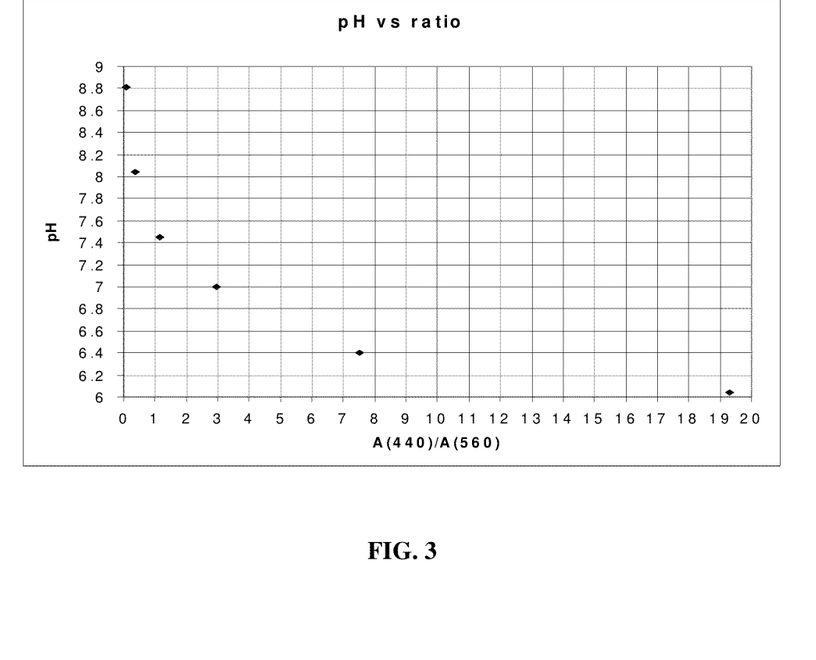
FIG. 3 is a calibration curve for dual-wavelength pH reader shown with pH as a function of absorbance ratio at the two wavelengths of the combination of light-emitting diodes, determined using a standard spectrophotometer.
Figure 4:
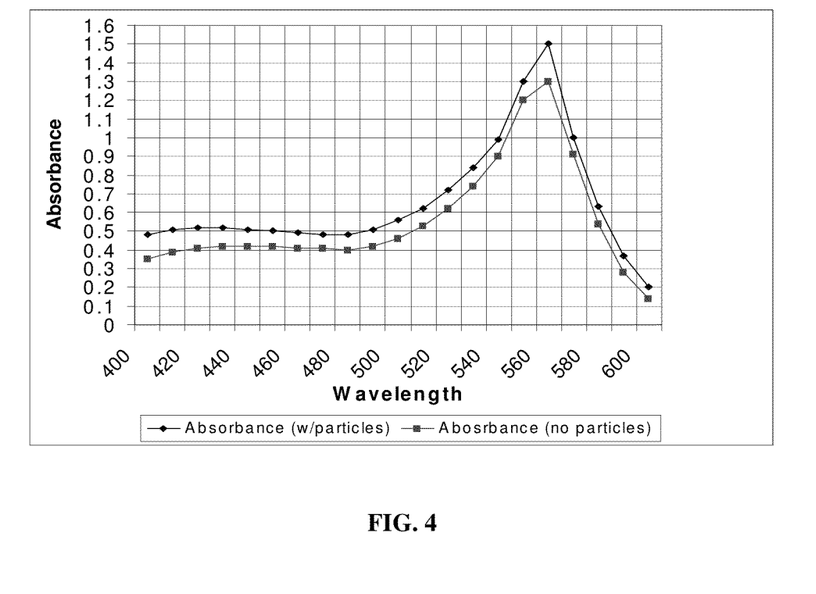
FIG. 4 is a graph showing absorbance spectra of phenol red in DMEM at pH 8.04 with (upper curve) and without (lower curve) 0.48 µm latex particles in suspension.

The original absorption spectra of phenol red solutions (FIG. 2), showed absorption maxima at 430 nm and 560 nm for phenol red in aqueous solution (Eagle's MEM, Minimum Essential Medium) and a systematic dependence of the ratio of these absorbances on pH. Absorption spectra for a current sample of actual medium (DMEM, Cat. No. 10316 Life Technologies, Inc.) were determined at 6 pH values. This solution had isosbestic absorbance at about 480 nm, with $A=0.35\pm0.03$—practically identical to the spectra in FIG. 2. The ratios of absorbances obtained by dividing absorption at 440 nm by that at 560 nm are graphed as a function of pH in FIG. 3, which is a calibration curve similar to one that is programmed into the embedded processor or an attached computer for the direct recording of pH. In view of the possibility that the presence of cells, which are light-scattering centers, could affect this calibration curve, spectra were determined in the presence and absence of 0.48 µm polystyrene latex particles (Interfacial Dynamics Corp., Eugene, Oreg., Cat. No. 10-11-33) suspended in DMEM at $2\times10^{-5}$ volume fraction. An example of such a pair of spectra (at pH 8.04) is shown in FIG. 4, from which it can be calculated that the added particles changed the absorbance ratio (440/560 nm) from 0.32 to 0.30, a change of less than 0.05 pH unit on the steep part of the calibration curve (FIG. 3). This indicates that corrections due to the presence of suspended cells or particles may be neglected in certain cases.

Example 2

Reduction to Practice of Embodiments

Figure 5:
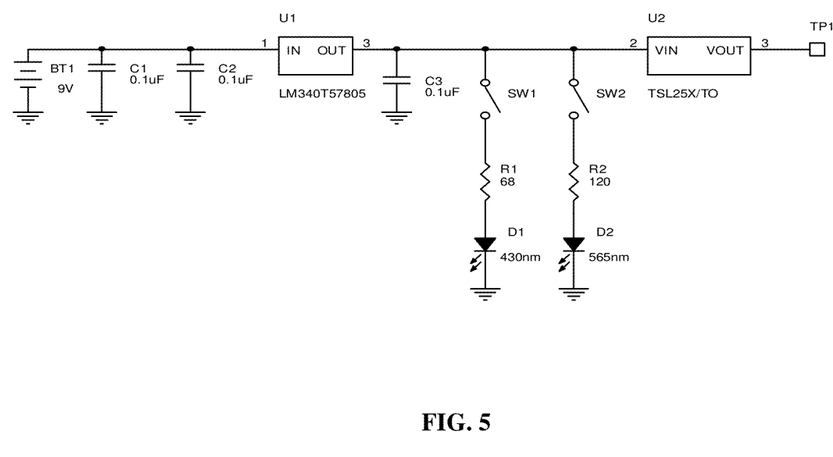
FIG. 5 is an example prototype pH Reader Circuit.

One possible photodetector is a side-looking electro-optic IC, which has an acceptable quantum efficiency response from 300-1050 nm and is available as the TAOS TSL25LR from Future Active (Indianapolis, Ind.). The volume of the pH reader for this test application is approximately 16 cm³, and the mass can be as little as 50 g. The power required by the LEDs, photodiodes, and their operational amplifiers is estimated at 80 mW. The output of the pH reader may be used to control medium pH inside a cell culture via gas composition regulation or by delivering fresh medium to the cell culture. This pH reader requires a holder that shields the solution container (flask, dish, test-tube, and the like) from ambient light, a photodetector and illuminators at two wavelengths mounted within this holder, and electronics for recording and displaying pH, time, and sample number. The surface mount LEDs selected for reduction to practice are blue and green LEDs, such as the LUMEX P/N SMF-2432SBC (blue) and the LUMEX P/N SMF-2432GC (green). A suitable circuit diagram for this pH reader is shown in FIG. 5. The volume of the commercial standalone version of the pH reader is expected to be approximately 50 cm$^3$, and the mass is likely to be below 100 g, and the power required is estimated at 80 mW.

An alternative emitter light source is a tri-color LED, such as the LUMEX part number SMLLXL5550SRSGSBW. The following advantages are realized by incorporating a tri-color LED: (1) each wavelength can be used from a single source, requiring only one control and power circuit; (2) the output spectra of the 565 and 430 nm diodes closely match the two peaks in the absorption spectrum of phenol red; (3) the pH reader can now serve as a generic spectrophotometer for reagent based analyses of medium composition, (4) the LED can also be operated at 660 nm, near the favored (red) wavelengths for turbidimetry (nephelometry) of biological suspensions, and (5) the red wavelength output can be used as calibration baseline when using phenol red, which does not absorb at this wavelength.

The photo detector board is based upon a PIN planar diffused, surface mount photodiode packaged in water clear resin (Photonic Detectors part number PDB-C154SM). The output current of this diode is converted to a voltage by an on-board MicroSIZE, Single-Supply CMOS Operational Amplifier (Burr-Brown part number OPA2337). The on-board amplifier prevents electromagnetic interference (EMI) noise from degrading the micro-ampere photo diode current as it is routed back to the reader electronics board.

The amplified output voltage is converted to a digital reading by a 10-bit analog to digital converter. To minimize signal noise and error due to digitization, the signal is averaged over eight separate readings for each wavelength. Further precision is gained by sampling the ambient light captured by the photodiode and subtracting it from the LED measurements. Mechanically, a collimator placed at both the emitter and receiver prevents noise from reflection and scatter of the emitted light in the sample.

Example 3

Calibration Curves for Cell Culture Media

Figure 6:
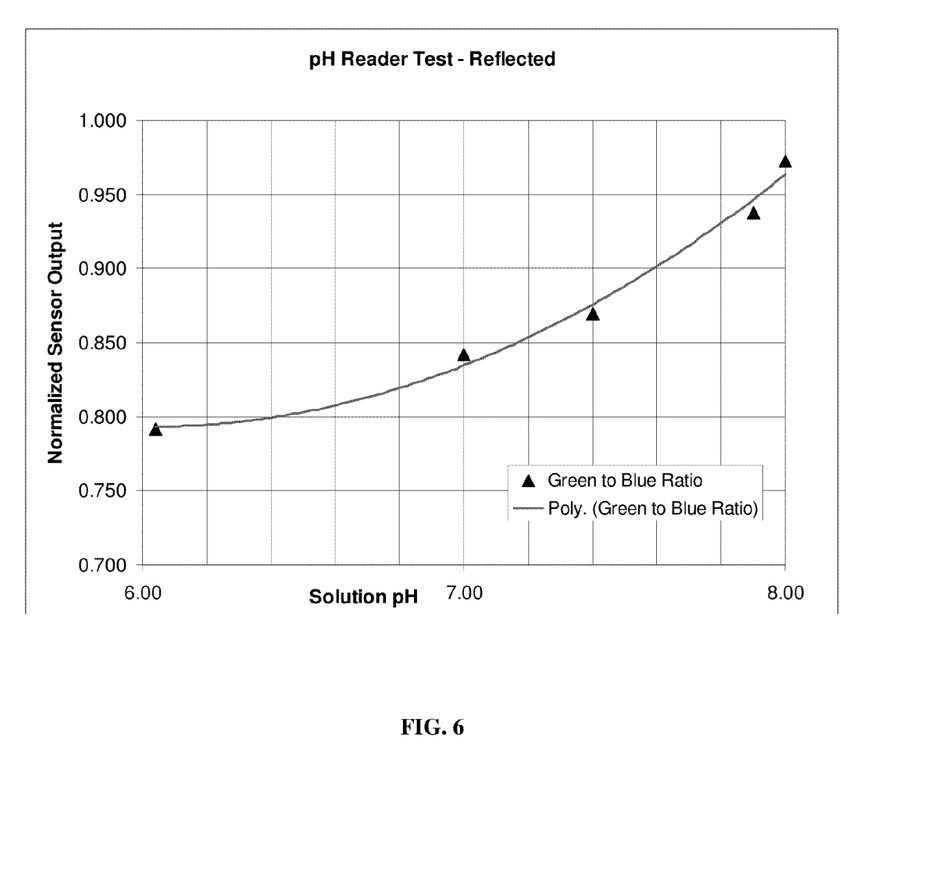
FIG. 6 is an output test data set from a pH Reader in reflection mode (the normalized sensor output is a ratio based on the amount of energy that is transmitted to the sensor and not the absorption of light by the fluid)
Figure 7:
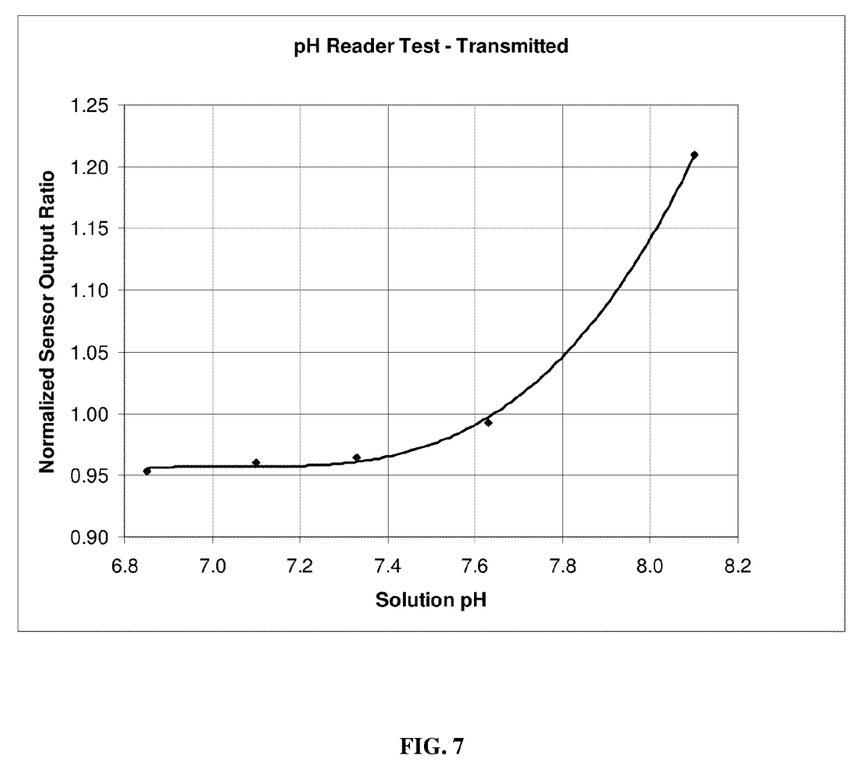
FIG. 7 is an output test data from a pH Reader in transmission mode (the normalized sensor output is a ratio based on the amount of energy that is transmitted to the sensor and not the absorption of light by the fluid)

Calibration curves have been produced using raw signal data, and the resulting calibration curves are satisfactory. Electronic outputs can be adjusted to make the ratio signal more or less sensitive to pH, thereby improving the accuracy of the pH reader. Appropriate positioning of the opto-electronic components in a mechanically robust housing ensures high repeatability. Calibration curves were developed using DMEM culture medium and OptiCell™ containers and are shown in FIG. 6 and FIG. 7 for operation in reflection and transmission mode, respectively. These are plots of the ratio of normalized output of the photodiode when illuminated at 440 nm to that at 565 nm, or I(440)/I(565), which is predicted to be an increasing function of pH, since A(440)/A(560) was shown to be a decreasing function of pH. The calibration curves are smooth monotonic functions, so that this method of reading pH is robust. These results also provide confidence that the Reader functions well in either reflection or transmissive modes.

Figure 8:
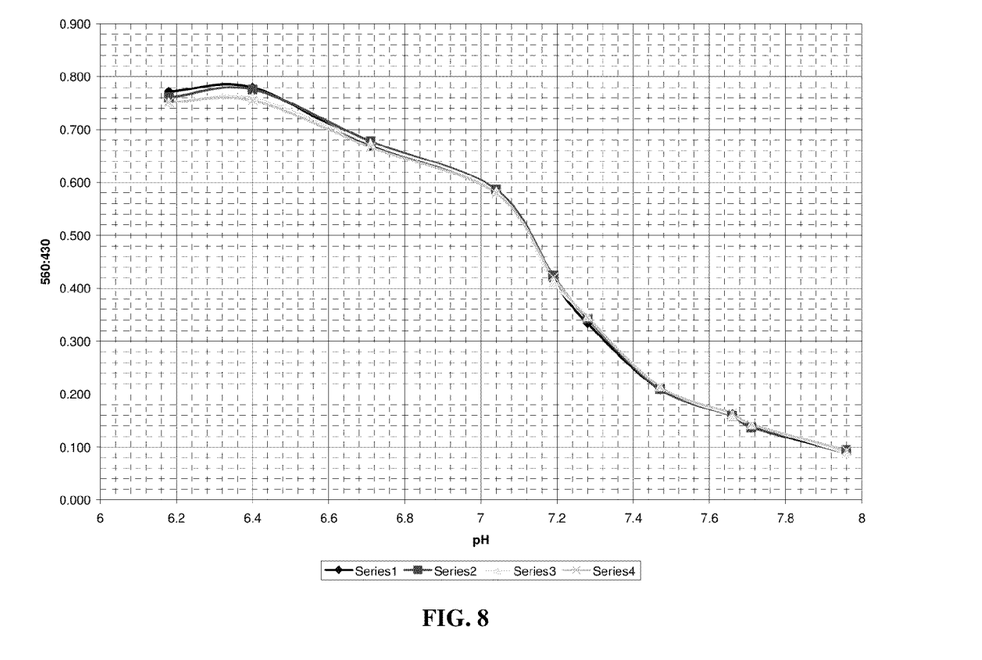
FIG. 8 is a plot of the ratio of 560 nm measurement to 430 nm measurement.

Ten Phenol Red solutions were mixed ranging from a pH of 6.18 to 7.96 (see FIG. 8). The pH of each solution was calibrated using an Orion Research Digital Ionalyzer 501 series pH meter. The pH solutions were injected into ten transparent "Multicult" slides, product of SHOT®, Inc. Two rounds of data were taken. Within each round, four series of data points were taken. The first round included eight slides starting with a low pH of 6.71. The second round of data used two slides with pH values of 6.18 and 6.4. Measurements recorded in FIG. 8 are voltage output values of the photodiode amplifier as sampled by the PIC18F8720 analog to digital converter.

Figure 9:
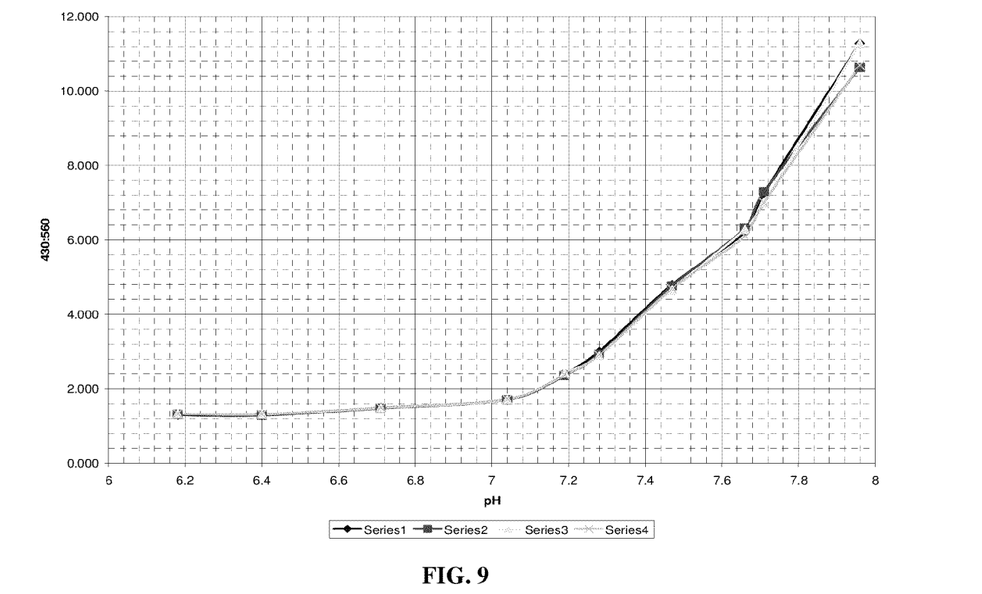
FIG. 9 is a plot of the ratio of 430 nm measurement to 560 nm measurement.

Considering Series 1, measurements of the 560 nm light intensity measurements decreased from 403 to 58 mV as the range of pH samples increased from 6.18 to 7.96. Over this same range, the measured 430 nm (Blue) light intensity increased from 522.58 mV to 654.84 mV. As additional series of data points were recorded, there was very little difference from series to series of the light intensity measurements. This confirms that the electronics hardware is capable of making repeatable measurements. The ratio of the 560 nm to 430 nm and 430 to 560 nm measurements (green/blue and blue/green) was determined for each series. FIG. 8 and FIG. 9 chart these ratios and demonstrate the repeatability of the pH system electronics. Using these data, a third-order polynomial calibration curve was constructed and is used by the attached computer with a graphical user interface (GUI) to convert raw light intensity readings to a pH value.

Analysis of capabilities has demonstrated the pH reader to be robust for cell culture medium samples containing phenol red. Its capabilities to report pH using other indicators such as methyl orange (Noller, 1957) and other solutions may be characterized separately.

Example 4

Automated Sequential pH Monitoring of Multiple Living Cell Cultures

Human mammary cancer cell line MDA-MB-231 was cultivated in Eagle MEM with pyruvate and non-essential amino acid supplement and 5% fetal bovine serum. Cells were harvested from stock cultures in polystyrene T-75 flasks using a cell-dispersal enzyme preparation, namely CELLSTRIP-PER™, CELLGRO product of Mediatech, Inc. (Herndon, Va.). A total of $10^5$ cells were plated on each of 6 "Multicult" slides (35 cm$^2$). Two control slides contained blank medium. One slide contained the same medium as that used for cells and the other contained unsupplemented DMEM (Dulbecco modification of Eagle's Minimum Essential Medium) in which 4.67 µm polystyrene latex beads were suspended. The standard concentrations of phenol red, bicarbonate buffer and phosphate buffer differ between the two media and are given in the following table.

Figure 10:
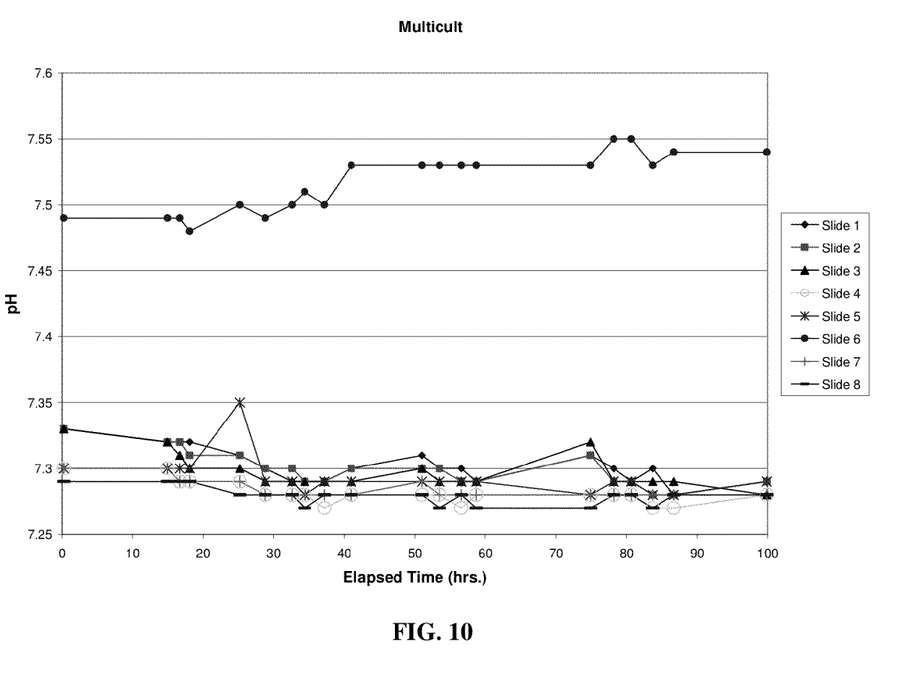
FIG. 10 is a plot of pH vs. time of culturing MDA-MB-213 cells in supplemented MEM (in the legend, "Slide 6" did not contain cells; pH was displayed directly by the Multicult pH reader in pH units using a calibration equation established using solutions of known pH).

| Medium | Bicarbonate concentration | Phenol Red Concentration | Phosphate Concentration |
| --- | --- | --- | --- |
| DMEM | 3700 mg/l | 15 mg/l | 125 mg/l NaH$_2$PO$_4$•H$_2$O |
| MEM | 2200 mg/l | 10 mg/l | 140 mg/l NaH$_2$PO$_4$•H$_2$O | pH readings were recorded every few hours with the slides in a water-saturated, 4.5% CO2, 37.5±0.2° C. atmosphere. Very small reductions in pH were observed in cultures that contained actively metabolizing cells, while slides that contained medium without cells had constant pH. The plots of pH vs. time for six cell cultures and one cell-free control (supplemented MEM as used for cells) are given in FIG. 10.

The pH of both control slides remained constant within ±0.02 pH unit, and the pH reader gave correct values for both DMEM and MEM, which, as noted in the above table, have different phenol red concentrations. The LED spectrophotometer readings were consistent with the fact that the DMEM sample had 50% more phenol red, some suspended microbeads and a higher pH than MEM on the basis of blue and green LED light transmission measurements, as indicated in the following table, which gives blue and green LED intensity measurements, in uncorrected arbitrary units, for DMEM and MEM maintained simultaneously under identical conditions.

| Medium | Blue Intensity | Green Intensity |
| --- | --- | --- |
| DMEM | 176 | 34 |
| MEM | 324 | 108 |
| MEM + cells | 345 | 112 |

While there has been described and illustrated particular embodiments of a novel apparatus and method, and in particular, a pH reader that can be used in cell cultures, it will be apparent to those skilled in the art that variations and modifications may be possible without deviating from the broad spirit and principle of the present invention, which shall be limited solely by the scope of the claims appended hereto.

We claim:

1. A method for non-invasively determining a chemical property of an aqueous solution comprising the steps of:
   providing a container having an interior portion and an exterior portion;
   providing, in said interior portion of said container, a colored solute having a light absorbance spectrum;
   providing a holder that shields said container from ambient light;
   providing at least one illuminator at said exterior portion of said container;
   transmitting light through said container with said at least one illuminator;
   providing a photodiode;
   measuring light absorbance of said colored solute at two different wavelengths with said photodiode; and
   utilizing a ratio of said light absorbance of said colored solute at said two different wavelengths to determine a chemical property of said aqueous solution.

2. The method of claim 1, wherein said chemical property is redox potential.

3. The method of claim 1, wherein said chemical property is pH.

4. The method of claim 3, wherein said colored solute is a pH indicator.

5. The method of claim 4, wherein said pH indicator is Phenol Red.

6. The method of claim 5, further comprising the step of providing an aqueous solution, wherein said aqueous solution is a solution capable of cultivating living cells of the type selected from the group consisting of plant, animal, fungal, or bacterial cells.

7. The method of claim 3, further comprising the step of converting said ratio to a hydrogen ion concentration.

8. The method of claim 3, further comprising the step of converting said ratio to a negative logarithm of hydrogen ion concentration.

9. The method of claim 3, further comprising the step of converting said ratio to a hydrogen ion concentration or pH using a calibrated circuit and a computer.

10. The method of claim 1, wherein one of said two different wavelengths is shorter than an isosbestic point wavelength of said colored solute.

11. The method of claim 1, wherein one of said two different wavelengths is longer than an isosbestic point wavelength of said colored solute.

12. The method of claim 1, wherein one of said two different wavelengths lies below and the other one of said two different wavelengths lies above an isosbestic wavelength.

* * * * *